United States Patent [19]

Bremer et al.

[11] Patent Number: 5,219,555
[45] Date of Patent: Jun. 15, 1993

[54] METHOD FOR LABELING PROTEINS WITH TECHNETIUM OR RHENIUM

[75] Inventors: Karl-Heinz Bremer, Bad Soden am Taunus; Ludwig Kuhlmann, Flörsheim am Main; Michael Magerstädt, Liederbach; Alexander Schwarz, Flörsheim am Main; Steinsträsser, Liederbach, all of Fed. Rep. of Germany

[73] Assignee: Hoechst Aktiengesellschaft, Frankfurt am Main, Fed. Rep. of Germany

[21] Appl. No.: 236,401

[22] Filed: Aug. 25, 1988

[30] Foreign Application Priority Data

Aug. 27, 1987 [DE] Fed. Rep. of Germany ....... 3728600

[51] Int. Cl.$^5$ .................... A61K 49/02; A61K 43/00; C07F 13/00
[52] U.S. Cl. .................... 424/1.1; 530/391.5; 530/391.7; 530/402; 530/304; 534/10; 534/14
[58] Field of Search .................... 424/1.1; 534/10, 14; 530/304, 391.5, 391.7, 402

[56] References Cited

U.S. PATENT DOCUMENTS

| 4,678,667 | 7/1987 | Meares et al. | 424/85.8 X |
| 4,818,813 | 4/1989 | Nowotnik et al. | 534/14 |
| 4,885,363 | 12/1989 | Tweedle et al. | 534/14 X |
| 5,087,696 | 2/1992 | Parker et al. | 424/11 |

FOREIGN PATENT DOCUMENTS 304780  3/1989  European Pat. Off. .

OTHER PUBLICATIONS

Franz, J. et al., "The Production of Tc-99m-Labeled . . . Chelating Agent", Nucl. Med. Biol., v. 14, No. 6, pp. 569–572, Jun. 1987.

Primary Examiner—Robert L. Stoll
Assistant Examiner—C. Sayala
Attorney, Agent, or Firm—Finnegan, Henderson, Farabow, Garrett and Dunner

[57] ABSTRACT

The invention relates to a method for labeling substances with—in particular radioactive—technetium or rhenium isotopes with the aid of N-substituted or C-substituted macrocyclic amine derivatives of the formula I and/or II

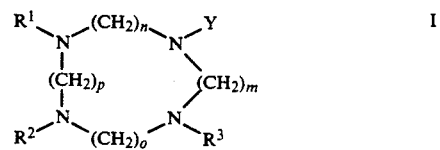

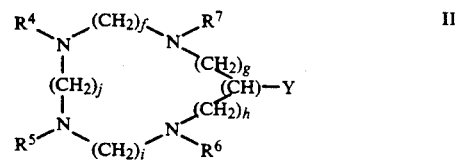

in which $R^1$–$R^7$, Y, m, n, o, p, f, g, h, i and j have the stated meanings, and to the use of these labeled substances, especially in medical diagnosis.

12 Claims, No Drawings

METHOD FOR LABELING PROTEINS WITH TECHNETIUM OR RHENIUM

The invention relates to a method for labeling substances with—in particular radioactive—technetium or rhenium isotopes using complexing agents, and to the use of these labeled substances.

There is a very wide variety of possible technical uses of radionuclides. They extend, for example, to testing a mixture, to the determination of quantities or volumes by dilution analysis, to the measurement of the flow rate and recording the hold-up time in continuously operating production plants.

However, it is usually insufficient merely to admix a radioactive nuclide, on the contrary it is necessary, for example when "following" a particular component in a system, to couple the radioactive nuclide physically, or even better chemically, to at least one compound of the component which is to be investigated and, where possible, to do this without affecting the physical and chemical properties of the relevant compound.

In recent years there has been a growth in the need to label chemical compounds with radioactive nuclides. It is now no longer possible to dispense with radioactively labeled substances, especially in the area of medical diagnosis, where pathological states can be revealed by substances which occur in the body only in ppm or in even lower concentrations.

In particular, technetium-99m has become the most important radionuclide in nuclear medical diagnosis because of its favorable physical properties (absence of corpuscular radiation, γ energy of 140 keV and half-life of 6 hours) and the low radiation dose associated therewith.

Technetium-99m can be obtained from nuclide generators and is initially in the form of pertechnetate which is suitable for scintiscanning the thyroid and brain, for example. Scintiscanning other organs using technetium-99m is possible with the aid of certain "transport substances" which are able, on the one hand, to bind technetium and, on the other hand, to accumulate the radionuclide in the target organ with high selectivity. In order to label the organ-specific "transport substance" with technetium-99m, it is first necessary to convert the pertechnetate which is eluted from the nuclide generator into a lower oxidation state. In this reduced form, technetium forms more or less stable compounds with the organ-specific substance. Employed for scintiscanning bone are, for example, Tc-99m/phosphorus acid derivatives, especially organic phosphonic acids. Thus, the labeling unit described in European Patent 2485 contains the sodium salt of 3,3-diphosphono-1,2-propanedicarboxylic acid as organ-specific "transport substance". European Patent 108,253 describes Tc-99m tri- and tetraphosphonic acids for the scintigraphic visualization of the RES, especially of the liver. The Tc-99m complex with diethylenetriaminepentaacetic acid (DTPA) is used for the diagnosis of renal diseases and pathological processes in the brain.

Special methods have been developed and described for labeling particular substances with technetium-99m and for preparing test kits suitable for routine clinical requirements. A method for producing labeling kits for macromolecules of biological interest, especially porphyrins, dextrans, cytochromes and myoglobin, is described (G. D. Zanelli, D. Ellison, M. P. Barrowcliffe, Nud. Med. Commun. 8, 199–206 1987), in which the substance which is to be labeled is lyophilized with p-aminobenzoic acid and a solution of $SnCl_2$ in hydrochloric acid. For the reconstitution and labeling of this kit, Tc-99m generator eluate which has previously been diluted with sufficient buffer solution, for example citrate/sodium chloride buffer pH 9.5, is added. However, this method is unsuitable for substances sensitive to acid.

In another method (E. K. J. Pauwels, R. I. J. Feitsma, Patent Application Int. Publication No. WO 86/03010), Tc-99m-pertechnetate is first reduced by heating at 140° C. in a strong solution of hydrochloric acid for four hours, and is bound to a compound which contains an amino group, for example dimethylformamide. The reactive Tc-99m-labeled intermediate, which precipitates as a sparingly soluble crystalline substance, is reacted with the compound which is to be labeled in a buffer solution, for example sodium carbonate solution, by incubation at room temperature for one hour. Although the method operates without tin, it is scarcely suitable for routine use because of the elaborate steps in the method.

Two different ways of labeling proteins, especially antibodies, are known. In the direct method, the reduced technetium-99m is bound to the protein by donor groups (amino, amide, thiol, etc.).

Methods of this type are described in European Patent 5638 and U.S. Pat. No. 4,478,815. In these, tin(II) salts are used in excess for the simultaneous reductive cleavage of disulfide bridges and reduction of the added Tc-99m-pertechnetate. In general, the incubation times required for cleavage of the —S—S-bond are relatively long (24 hours), with F(ab')$_2$ fragments being partially cleaved to F(ab) fragments. Recent statements in the literature (for example Journal of Nuclear Medicine 27 (1986), pages 685–93 and 1315–20, and International Journal of Nuclear Medicine Biology 12 (1985) pages 3–8) show that the ratio of the two fragments depends on the "stannation reaction", and that the ratio of the two components no longer changes to a noteworthy extent after the Tc-99m-labeling, with the main component being Tc-99m-labeled F(ab'). It was necessary in all cases subsequently to purify the labeled F(ab') fragment, because quantitative conversion of the pertechnetate was not achieved despite a reaction time of at least 30 minutes.

In a rapid chemical method for the Tc-99m-labeling of human plasma proteins (D. W. Wong, F. Mishkin, T. Lee, J. Nucl. Med. 20, 967–72, 1979) pertechnetate is first reduced by tin(II) ions in acid solution, and the reduced technetium is then reacted with the protein.

Stable labeling of substances with radioisotopes can be achieved with the assistance of bifunctional complexing agents.

In U.S. Pat. No. 4,479,930 the cyclic anhydrides of DTPA and EDTA are mentioned as chelating agents not only for In-111 and Ga-67 but also for Tc-99m. European Patent 35765 mentions the use of deferoxamine as agent for complexing technetium-99m to proteins. In the International Patent Application WO 85/3063, the partially reduced disulfide bridges in the antibody are reacted with the sodium salt of tetrachloronitridotechnetate, which needs to be prepared beforehand by reaction of pertechnetate with sodium azide. In the European Patent Application 194853, free mercapto groups which have likewise been generated by a reduction in antibody fragments are used to bind [(7-maleimidoheptyl)imino-bis(ethylenenitrilo)] tetraacetic acid as a chelate complex. The coupling of the complex to the antibody takes place by the reaction of the SH groups with the double bond in the maleinimide part of the complex compound, while the radioactive metal ion is complexed via the nitrilodiacetic acid residues.

Metallothionein, a metal-binding protein with a molecular weight of 6000 and a high content of cysteine in the molecule, has been introduced as a complexing agent in antibodies (G. L. Tolman, R. J. Hadjian, M. M. Morelock et al., J. Nucl. Med. 25, 20, 1984). It was possible to label the antibody-metallothionein conjugate with technetium by exchange with Tc-99m glucoheptonate. However, exchange was incomplete so that subsequent purification was necessary. Several bisthiosemicarbazone ligands have likewise been described as bifunctional chelating agents (Y. Arano, A. Yokoyama, H. Magat et al., Int. J. Nucl. Med. Biol. 12, 425–30, 1986). p-Carboxyethylphenylglyoxal di(N-methylthiosemicarbazone) has been conjugated with human serum albumin. The Tc-99m-labeled 1:1 complex exhibited a certain instability, whereas complexes with a higher ratio than 1:1 showed increased liver accumulation. Coupling of a diamidedimercaptide $N_2S_2$ ligand to proteins (A. R. Fritzberg, S. Kasina, J. M. Reno et al., J. Nucl. Med. 27, 957–958, 1986) takes place via an additional functional group. Thus, for example, 4,5-di(S-ethylcarbonylmercaptoacetamido)pentanoyl-N-hydroxysuccinimide was reacted with an antimelanoma antibody. The resulting conjugate was incubated with Tc-99m tartrate solution at pH 8 and 50° C. After one hour, 78% of the technetium had been transferred from the tartrate to the antibody.

In order to be able to use technetium-99m widely in diagnosis, it is necessary to transport this nuclide selectively into the organ which is to be investigated. The technetium-99m should be rapidly eliminated again from other organs or organ systems, or should not be introduced in the first place, in order to avoid all unnecessary exposure of the patient to radiation. The substances hitherto mainly used for this purpose are those which can be directly labeled with technetium-99m and have high organ specificity. However, there is in addition a number of substances which cannot be directly labeled although they have high organ specificity. These may be proteins (fibrinogen, human serum albumin), enzymes (streptokinase, lactic dehydrogenase), sugars (dextran, glucose) or else polymers. They also include low molecular weight substances such as, for example, fatty acids which, owing to the high energy requirements of the heart, accumulate in the myocardial tissue. In order to be able to label these substances, they are coupled to complexing agents which in turn are able strongly to bind technetium-99m.

Complexing agents known to be suitable for the complexing of technetium and rhenium isotopes are macrocyclic amines, including cyclams. The complexation yield for the technetium-cyclam complex is 99% under suitable conditions. Details of technetium-amine complexes are given in D. E. Troutner, J. Simon, A. R. Ketring, W. A. Volkert, R. A. Holmes, J. Nucl. Med. 21 (1980), 443 or S. A. Zuckman, G. M. Freeman, D. E. Troutner, W. A. Volkert, R. A. Holmes, D. G. van der Keer, E. K. Barefiled, Inorg. Ch. 20 (1981), 3386 or J. Simon, D. Troutner, W. A. Volkert, R. A. Holmes, Radiochem. Radioanal. Lett. 47 (1981), 111. Substituted cyclams are also known, substituted both on the 1-nitrogen and on the 6-carbon (A. R. Ketring, D. E. Troutner et al., Int. J. Nucl. Med. Biol. 11 (1984), 113 or J. Simon, Diss. Abstr. Int. B42 (1981), 645 or M. Struden, T. A. Kaden, Helv. Chim. Acta 69 (1986), 2081 or E. Kimura, R. Machida, M. Kodama, J. Am. Chem. Soc. 106 (1984), 5497).

All attempts to date to conjugate amine and other ligands to proteins (see Fritzberg et al., J. Nucl. Med. 27 (1986), 957 or Tolman et al., J. Nucl. Med. 25 (1984), 20 or Arano et al., Int. J. Nucl. Med. Biol. 12 (1986) 425) have resulted in products which did not meet, or met only partially, the high demands on in vivo stability.

A method which permits substances to be labeled with technetium or ruthenium isotopes with the aid of substituted macrocyclic amines, especially cyclams, has now been found.

The "substances" which can be labeled with the aid of the method according to the invention are primarily to be understood to be those compounds which can be used in medical diagnosis as "transport substances", that is to say usually compounds which have a high organ specificity, such as antibodies, antibody fragments such as F(ab')$_2$ or F(ab') fragments, proteins such as fibrinogen or human serum albumin, a hormone steroids, lipids, enzymes such as streptokinase or lactic dehydrogenase, sugars such as dextran or glucose, or else polymers, the polymers containing at least one side-chain of the formula —B—NH$_2$, —B—COOH, —B—NH—NH$_2$, —B—COCl or—B—OH, where B represents an o-, m- or p-arylene radical or an alkylene chain having 1 to 40 carbon atoms which, in the case of a C$_2$–C$_{40}$-alkylene chain, can also be interrupted by an —NH—, —NH—CO—, —CO—NH—, —CO—O— or —O—CO— unit, and where the polymers have a molecular weight of 1000 to 200,000 daltons. However, on the other hand, it is also possible in general to label with the aid of the method according to the invention those substances which react with the functional group on the side-chain of the macrocyclic amine with the formation of a chemical bond. Of interest in this context is the "monitoring" of chemical substances in production plants, the determination of their concentration, flow rate, hold-up time etc.

Hence the invention relates to a method for labeling substances with technetium or rhenium isotopes, which comprises a) the substance which is to be labeled being reacted with an N-substituted or C-substituted macrocyclic amine derivative of the formula I and/or II

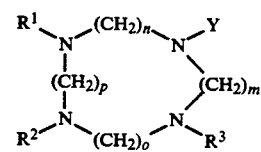

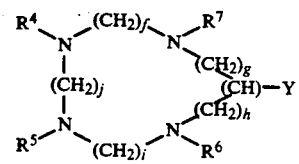

in which $R^1$, $R^2$, $R^3$, $R^4$, $R^5$, $R^6$ and $R^7$ are identical or different and denote hydrogen, C$_1$–C$_4$-alkyl or aryl or aryl-C$_1$–C$_4$-alkyl, and m, n, o, p, f, h, i and j are identical or different and denote 1, 2, 3 or 4 and g denotes 0, 1, 2, 3 or 4, and Y denotes a group of the formula —X–NH$_2$, —X—NCS, —X—COOH, —X—OH, —X—N$_2^+$ or —X—COCl or a group of the formula —X—Z, where Z denotes fluorine, chlorine, bromine or iodine, and X denotes an alkylene group having 1 to 40 carbon atoms, or X denotes an ortho-, meta- or para-phenylene or an ortho-, meta- or para-phenylenemethyl group, and the resulting compound being labeled with technetium-99m or rhenium-186 or -188 by adding to it pertechnetate-99m or perrhenate-186 or -188 and a reducing agent for pertechnetate-99m or perrhenate-186 or -188, or comprises b) initially preparing the technetium-99m and/or rhenium-186 or -188 complex by a reaction of a compound of the formula I and/or II with pertechnetate-99m and/or perrhenate-186 or -188 and a reducing agent for pertechnetate-99m and/or perrhenate-186 or -188, and subsequently reacting this technetium-99m and/or rhenium-186 or -188 complex with the substance which is to be labeled.

In particular, the invention relates to a method for labeling substances with technetium or rhenium isotopes, in which are used macrocyclic amines of the formula I and/or II in which R$^1$, R$^2$, R$^3$, R$^4$, R$^5$, R$^6$ and R$^7$ are identical or different and denote hydrogen or C$_1$–C$_4$-alkyl, and n, o, p, f, i and j are identical or different and denote 2 or 3, and g denotes 0, 1 or 2, and h denotes 1 or 2, and Y denotes a group of the formula —X—NH$_2$, —X—NCS, —X—COOH, —X—OH, —X—N$_2^+$ or —X—COCl or a group of the formula —X—Z, where Z denotes fluorine, chlorine, bromine or iodine, and X denotes an alkylene group having 1 to 20 carbon atoms.

A very particularly preferred method for labeling substances with technetium or rhenium isotopes entails use of macrocyclic amines of the formula I and/or II in which R$^1$, R$^2$, R$^3$, R$^4$, R$^5$, R$^6$ and R$^7$ denote hydrogen, and m, p and j denote 3, and n, o, f and i denote 2, and g and h denote 1, and Y denotes a group of the formula —X—NH$_2$, where X denotes an alkylene group having 1 to 15 carbon atoms.

The invention furthermore relates to the use of the labeled substances, especially in medical diagnosis.

Aryl is to be understood to be phenyl and naphthyl, in particular phenyl. Alkyl groups having more than 2 carbon atoms can be both straight-chain and branched. The alkylene group X is preferably a straight-chain alkylene having up to 40 carbon atoms, preferably up to 20, particularly preferably up to 15 carbon atoms.

In the method according to the invention, either a N-substituted or a C-substituted macrocyclic amine derivative which has a functional group at the end of the substituent is bonded with the aid of this functional group to the substance which is to be labeled. Where appropriate after suitable purification of the conjugate (for example by ultrafiltration or dialysis in the case of proteins or polymers, or by column chromatography in the case of lower molecular weight substances such as steroids or lipids), technetium-99m in the form of pertechnetate, or rhenium-186 or -188 in the form of perrhenate, and a suitable reducing agent for reducing the pertechnetate or perrhenate to the oxidation state required for the complexation, are added in arbitrary sequence or together. The labeled substrate is purified again where appropriate.

Another possible alternative is initially to generate the technetium or rhenium complex of the cyclic amine and then to react this complex with the substance to give the conjugate. In this case, the complexation and reduction take place as described above. The complexation reaction is preferably carried out at basic pH (7 to 14). Macrocyclic amines of the formula III or IV

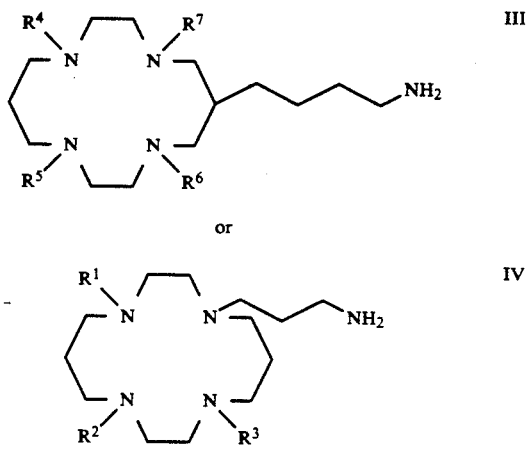

are preferably employed as complexing agents.

The macrocyclic amines of formula I or II are prepared most straightforwardly by reactions of bis(ω-aminoalkyl)amines which are initially tritosylated, and subsequently converted into the disodium salt, with triply tosylated α,ω-dihydroxydialkylamine, followed by a detosylation. A corresponding synthetic method is described by J. Richman and T. Atkins in J. Am. Chem. Soc. 96 (1974), 2268. The radicals R$^1$ to R$^7$ can be introduced by methods known from the literature, for example by alkylation with alkyl halides.

The coupling of the exocyclic side-chain having a terminal reactive group onto an NH group is carried out, for example, by reacting the macrocyclic amines with ω-nitroalkylcarbonyl halides, preferably chlorides, and a subsequent hydrogenation, with the carbonyl and the nitro group being reduced to a CH$_2$ and NH$_2$ group, respectively. An analogous reaction with bromides is described, for example, in A. R. Ketring, D. E. Troutner et al., Int. J. Nucl. Med. Biol., 11 (1984), 113.

An example of a possible procedure for the preparation of the C-substituted macrocyclic amines is the following: N,N'-di(aminoalkyl)-α,ω-alkanediamine is converted with tosyl chloride and sodium alcoholate into the tetratosyl disodium derivative, which is reacted with a (preferably) tosylaminoalkyl-α,ω-alkyl tosylate to give the C-aminoalkyl-substituted tetraazacycloalkane.

All these variants of the synthesis of macrocyclic amines are based, to a greater or lesser extent, on the method of J. Richman and T. Atkins (see loc. cit.). A very wide variety of macrocyclic amines can be prepared by simple modifications of this method - for example those with alkylene chains of different lengths or else those with C-substituted exocyclic side-chains.

Most of the starting compounds described above, for example many N,N'-di(aminoalkyl)-α,ω-alkanediamines and many "Y"-substituted α,ω-alkanediols, can be bought or prepared in a straightforward manner.

The pertechnetate or the perrhenate can be reduced by methods known from the literature, preferably with a tin(II) compound. The reduction is particularly preferably carried out with a complex-stabilized tin(II) salt by a "labeling method" as proposed in German Offenlegungsschrift DE-A 3728599. This entails first the tin-(II) compound being mixed with a complexing agent, preferably a phosphorus compound such as a phosphonate or pyrophosphate, which ensures that the tin compound remains in solution, especially in the physiological pH range. This complex-stabilized tin(II) salt solution can then be added either to the substance which is to be labeled, followed by addition of the pertechnetate or perrhenate solution, or else to a mixture of the substance which is to be labeled and of the pertechnetate or perrhenate solution.

The invention is explained in detail hereinafter by means of examples and is defined in the patent claims.

EXAMPLE 1

Preparation of the N-substituted cyclam 1-(3-aminopropyl)-1,4,8,11-tetraazacyclotetradecane

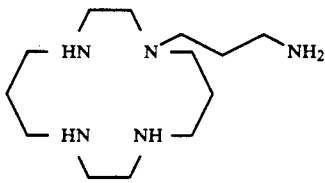

a) 5 g of 3-nitropropionic acid are dissolved in about 40 ml of SOCl$_2$ and refluxed for 2 h. The SOCl$_2$ is removed in vacuo, and the product is dried in vacuo.

b) 6.6 g of cyclam (1,4,8,11-tetraazacyclotetradecane) and 0.18 g of Na$_2$CO$_3$ are introduced into 100 ml of CHCl$_3$ at 0° C. 0.45 g of 3-nitropropionyl chloride is added dropwise to this mixture. After the mixture has been stirred for 24 h it is refluxed for 8 h, and then the solution is evaporated and dried. The residue is taken up in aqueous HCl (pH 1.5), and the solution is extracted twice with 100 ml of diethyl ether each time. Evaporation to dryness is repeated. The residue is added to 100 ml of 40% NaOH, and the mixture is triturated and extracted twice with 50 ml of (C$_2$H$_5$)$_2$O each time. The ether phase is discarded. Extraction of the base twice with 100 ml of ethyl acetate provides, after removal and drying of the organic phase, a yellowish residue from which excess cyclam is sublimed out at 100° C./0.1 torr. The 3-nitropropionylcyclam is obtained as a hygroscopic yellowish solid after a crystallization from H$_2$O (decomposition at 175° C.), characterized by C, H and N analysis, mass spectrum and $^1$H NMR and IR.

Yield: 0.22 g (25%).

An aqueous solution of 0.2 g of 3-nitropropionylcyclam and ammonia (pH 10) are added, at 0° C., to an aqueous H$_2$-saturated solution of a catalyst composed of 10% Pt on active charcoal. The mixture is brought under an H2 atmosphere. The reaction is complete when no more H2 is consumed. The solution is filtered through kieselguhr and freeze-dried. The 1-(3-aminopropyl)-1,4, 8,11-tetraazacyclotetradecane is obtained as a yellowish solid and characterized by C, H and N analyses, mass spectra and $^1$H NMR.

Yield: 100 mg (=58% of theory).

EXAMPLE 2

Preparation of 6-(4-aminobutyl)-1, 4, 8, 11-tetraazacyclotetradecane

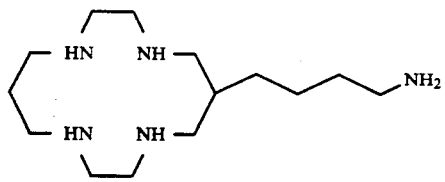

a) Synthesis of TsHN-(CH2)2-NTs-(CH2)3-NTs-(CH2)2-NHTs 2 g of N,N'-di(aminoethyl)-1,3-propanediamine are dissolved together with 2 g of NaOH in 250 ml of water, and 9.4 g of p-toluenesulfonyl chloride dissolved in 80 ml of diethyl ether are added dropwise, with vigorous stirring at room temperature, in 30 minutes. after 1 h, the ether is slowly evaporated by passing in N$_2$, during which the tetratosylated product precipitates. It is filtered off from the solution, carefully washed copiously with water and dried in vacuo. The colorless solid product can be identified by its $^1$H NMR spectrum in CDCl$_3$.

Yield 6.5 g (67% of theory).

b) Synthesis of NaTsN-(CH$_2$)$_2$-NTs-(CH$_2$)$_3$-NTs-(CH$_2$)$_2$-NTsNa

The tetratosylate (6.5 g) is introduced into about 200 ml of C$_2$H$_5$OH, and a solution of 0.4 g of Na in 40 ml of C$_2$H$_5$OH is added dropwise. After the solution has been refluxed for 1 h it is evaporated in a rotary evaporator, and the sodium salt of the tetratosylate is dried in vacuo. Yield 6.8 g, sublimation/decomposition at 110° C.

c) Synthesis of diethyl 2-(3-cyanopropyl)malonate 5.2 g of NaH are washed 3 times with petroleum ether and then taken up in 300 ml of THF. At 0° C., diethyl malonate (16 g) is slowly added dropwise under nitrogen, then the mixture is warmed to room temperature, refluxed for 2 h and then cooled to 0° C. again, followed by dropwise addition of 4-bromobutyronitrile (8.2 ml) in about 20 ml of tetrahydrofuran. After the mixture has been stirred at room temperature for 15 hours it is refluxed for 1 h, cooled and filtered to remove NaBr, and the filtrate is evaporated to an oil. About 50 ml of CH$_2$Cl$_2$ are added and then the mixture is extracted twice with 100 ml of H$_2$O each time, and then the organic phase is separated off, dried over MgSO$_4$ and evaporated. The oily residue is distilled in vacuo and distils at 105°-112° C./0.1-0.5 mm Hg. $^1$H NMR in CDCl$_3$ shows the product. Yield 6.02 g (32% of theory).

d) Synthesis of 2-(4-aminobutyl)-1,3-propanediol 6 g of diethyl 2-(3-cyanopropyl)malonate are added dropwise, at −10° C., to a suspension of 3 g of LiAlH$_4$ in 100 ml of dry diethyl ether under N$_2$. The mixture is slowly warmed to room temperature and then refluxed for 3 h. After renewed cooling to −10° C., the excess hydride is decomposed with water. The precipitate is removed on a frit and washed several times with diethyl ether. The ether solution is dried over MgSO$_4$, filtered and evaporated in a rotary evaporator. Yield 0.66 g of 2-(4-aminobutyl)-1,3-propanediol, detectable in the $^1$H NMR and by C and H analysis. Glassy solid, melting point 126° C. (honey-like above 60° C.).

e) Conversion of the 2-(4-aminobutyl)-1,3-propanediol into the O,O,N-tritosylate The 2-(4-aminobutyl)-1,3-propanediol (0.6 g) is introduced into 50 ml of $CH_2Cl_2$, then 1.22 ml of pyridine are added, and 2.35 g of TsCl in 20 ml of $CH_2Cl_2$ are added dropwise to this solution at 20° C. in 30 minutes. After the mixture has been stirred for 20 hours it is washed several times with 2N HCl, and the organic phase is separated off, dried over $MgSO_4$ and evaporated in a rotary evaporator. The product - tosylated 2-(4-aminobutyl)-1,3-propanediol - can be purified by column chromatography with butanol/silica gel. Detection by C, H, and N analysis and $^1H$ NMR.

Yield: 2.36 g (95%).

f) Cyclization 1.74 g of the disodium salt from example 2b) are introduced into 5 ml of dimethylformamide, heated to 100° C., and the diol tritosylate from example 2e), dissolved in 10 ml of DMF, is added dropwise at 100° C. After the solution has been stirred at 100° C. for 4 h it is cooled to room temperature and then stirred for a further 15 h. After addition of about 10–15 ml of $H_2O$, tosylated 6-(4-aminobutyl)-1,4,8,11-tetraazacyclotetradecane precipitates out and is washed several times with water and dried.

Yield 1.43 g (66% of theory). Characterization by $^1H$ NMR in $CDCl_3$. Decomposition above 132° C., completely decomposed at 236° C.

g) Detosylation

The pentatosylate from example 2f) (1.4 g) is added to 20 ml of concentrated $H_2SO_4$ and mixed at 95° C. As soon as a sample is soluble in water, the mixture is cooled to $-10°$ C., and the product is precipitated with 20 ml of diethyl ether. After filtration, the gray, dried solid is added to 40% NaOH (40 ml) and extracted several times with diethyl ether. 6-(4-aminobutyl)-1,4,8,11-tetraazacyclotetradecane is obtained from the ether and can be purified by chromatography.

Yield: 0.3 g (85%). Characterization by C, H and N analysis, mass spectrum and $^1H$ NMR.

EXAMPLE 3

Synthesis of 6-(11-hydroxyundecyl)-1,4,8,11-tetraazacyclotetradecane a) Synthesis of methyl 11-bromoundecanoate 26 5 g (0.10 mol) of 11-bromoundecanoic acid are introduced into a three-neck flask with condenser, bubble counter, thermometer and dropping funnel, and 17.8 g (0.15 mol) of thionyl chloride are added dropwise while cooling in ice so that the temperature does not exceed 20° C. The mixture is then heated at 70° C. in a water bath and stirred until evolution of gas (HCl, $SO_2$) is complete. The unconsumed thionyl chloride is condensed in a cold trap under waterpump vacuum.

3.52 g (0.11 mol) of anhydrous methanol are added to the unpurified 11-bromoundecanoyl chloride, and the mixture is stirred in a water bath at 40° C. until the evolution of hydrogen chloride is complete. The resulting crude product is distilled through a Vigreux column (boiling point 105° to 108° C./0.1 mbar).

Yield: 26.19 g (93.8%) characterization by $^1H$ NMR, mass spectrum and C and H analysis b) Synthesis of methyl 12,12-dicyanododecanoate 100 ml of anhydrous tetrahydrofuran are introduced into a three-neck flask with stirrer, reflux condenser and dropping funnel, and 11.22 g (0.10 mol) of potassium tert.butylate are suspended with stirring. 6.61 g (0.10 mol) of 1,1-dicyanomethane dissolved in 20 ml of anhydrous tetrahydrofuran are added dropwise to this, while cooling in ice so that the temperature does not rise above 10° C. Subsequently, 28.0 g (0.10 mol) of methyl 11-bromoundecanoate are added, and the mixture is refluxed for 15 h. After cooling, the precipitated potassium bromide is filtered off, the filtrate is evaporated to dryness in a rotary evaporator, the residue is taken up in 100 ml of diethyl ether, and the solution is washed three times with 50 ml of water each time. The ethereal phase is dried over sodium sulfate and evaporated to dryness in a rotary evaporator, and the resulting crude product is distilled in a short-path distillation apparatus (boiling point 150 to 160° C./0.6 mbar).

Yield: 25.56 g (96%).

Melting point: 36° C., characterization by $^1H$ NMR, mass spectra and C, H and N analysis.

c) Reduction of methyl 12,12-dicyanododecanoate to 12-aminomethyl-13-aminotridecanol dihydrochloride 5 g of methyl 12,12-dicyanododecanoate (19 mmol) are dissolved in 200 ml of tetrahydrofuran in a two-neck flask with dropping funnel and reflux condenser with a bubble counter on top, and the solution is cooled to 0° C. 200 ml of a 1 molar solution of $BH_3$-THF complex in tetrahydrofuran are added dropwise to this. The mixture is then refluxed for 3 hours, cooled to room temperature, stirred for 1 to 2 hours, again cooled to 0° C., and dry methanol (about 100 to 150 ml) is cautiously added dropwise in order to decompose excess borane. The solvent is removed in a rotary evaporator, and then the gummy residue is taken up in about 100 ml of methanol. The methanol is again removed in a rotary evaporator, and the residue is taken up once more in 100 ml of methanol, and the solution is evaporated in a rotary evaporator. Dry ethanol is added to the residue until a clear solution is just produced. This is cooled to $-10°$ C. and treated with HCl gas for one hour. The mixture is then refluxed for 5 h. It is cooled once again to $-10°$ C., and the solution is saturated with gaseous HCl. After cooling at $-18°$ C. in a tightly closed flask overnight, the product separates out as a white crystalline precipitate. More crude product can be obtained by evaporating the solution in a rotary evaporator. The crude product is purified by washing with a little cold ethanol and then drying in vacuo.

Yield: 5.1 g (79%).

Characterization by $^1H$ NMR, IR and C, H and N analysis.

d) Synthesis of N,N'-bis(p-toluenesulfonyl)-12-aminomethyl-13-aminotridecanol 0.9 mmol of the substance from example 3c is dissolved in about 5 ml of pyridine, and the tosyl chloride is added as the solid while stirring at 20° C. After the mixture has been stirred at 20° C. for 20 h, the solvent is evaporated, and the residue is taken up into 2 N HCl. The acidic solution is extracted twice with diethyl ether, and the ether phase yields 250 mg of pale yellowish solid (50%). Characterization by $^1H$ NMR.

e) Synthesis of N,N'-disodium-N,N'-bis(p-toluenesulfonyl)-12-aminomethyl-13-aminotridecanol 14 mg of Na are dissolved in 5 ml of ethanol, and the solution is added to a solution of 200 mg of the substance from example 3d in 10 ml of ethanol. After the mixture has been stirred at room temperature for 2 h it is refluxed for 2 h. The solution is evaporated in a rotary evaporator, and the residue is dried in vacuo.

Characterization of the product (226 mg, 97% of theory) by ¹H NMR (colorless solid).

f) Preparation of N,N'-bis(p-toluenesulfonyl)-N,N'-bis(2-toluenesulfonyloxyethyl)-1,3-propanediamine from N,N'-bis(2-hydroxyethyl)-1,3-propanediamine 4 g of N,N'-bis(2-hydroxyethyl)-1,3-propanediamine are dissolved in 100 ml of CH₂Cl₂ and, at 20° C., 7.8 g of pyridine are added. Then 18.8 g of tosyl chloride in 70 ml of CH₂Cl₂ are added. After 50 h at 20° C., 2 N HCl (100 ml) is added to the solution, which is then extracted 3 times with 50 ml of CH₂Cl₂ each time. The organic phase is dried over Na₂SO₄, filtered and evaporated, and the solid residue is taken up again in 50 ml of 2 N HCl, and the solution is extracted 3 times with 50 ml of diethyl ether each time and then twice with 50 ml of ethyl acetate each time. The ethyl acetate fraction is dried over Na₂SO₄, filtered and evaporated in a rotary evaporator to yield 5.7 g (30% of theory) of a yellowish solid which was characterized by ¹H NMR and thin-layer chromatography.

g) Cyclization of N,N'-disodium-N,N'-bis(p-toluenesulfonyl)-12-aminomethyl-13-aminotridecanol with N,N'-bis(p-toluenesulfonyl)-N,N'-bis[2-(p-toluenesulfonyloxy)-ethyl]-1,3-propanediamine to give 6-(11-hydroxyundecyl)-1,4,8,11-tetra(p-toluenesulfonyl)-1,4,8,11-tetraazacyclotetradecane

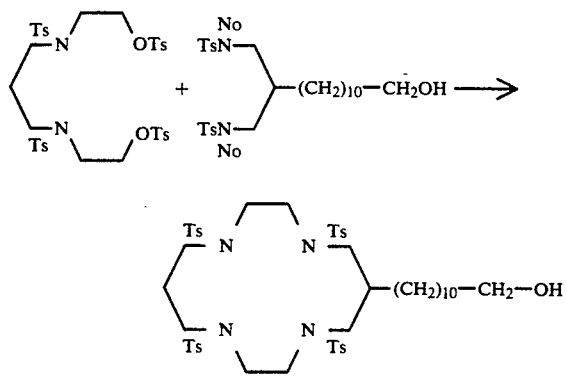

A solution of 220 mg of the substance from example 3e in 10 ml of dimethylformamide is added dropwise, at 100° C.,to a solution of 288 mg of the substance from example 3f in 10 ml of dimethylformamide. After the mixture has been stirred at 100° C. for 4 h it is cooled to room temperature, and the crude product is precipitated with water.

The yellow, gummy solid is washed with water (several times) and then reprecipitated from acetone/water. The dried solid (140 mg, 38%) can be further purified by column chromatography on silica gel 60 using ether as mobile phase (Rf=0.72).

h) Detosylation of 6-(11-hydroxyundecyl)-1,4,8,11-tetra(p-toluenesulfonyl)-1,4,8,11-tetraazacyclotetradecane with H₂SO₄ to give 6-(11-hydroxyundecyl)-1,4,8,11-tetraazecyclotetradecane

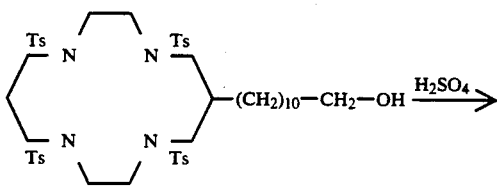

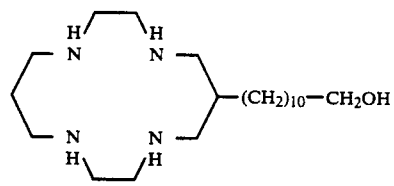

140 mg of the substance from example 3g are suspended in about 5 ml of concentrated H2SO4 and stirred at 100° C. for several hours. The reaction is complete when a sample of the solution is soluble in water. It is then cooled to 4° C., and the polysulfate salt is precipitated by addition of diethyl ether, and is filtered off under N₂. The product is added to 40% NaOH, and then 6-(11-hydroxyundecyl)-1,4,8,11-tetraazacyclotetradecane is extracted with benzene. The product is characterized by ¹H NMR, mass spectrum, C, H and N analysis and IR spectrum after the solvent has been removed in vacuo and the residue has been dried in vacuo.

Yield: 45 mg (87%).

EXAMPLE 4

Labeling with technetium-99m of a polymer which contains COOH groups using the bifunctional cyclam from example 1 a) Reaction of monomethoxypolyethylene glycol monocarboxylate with 1-(3-aminopropyl)-1,4,8,11-tetraazacyclotetradecane

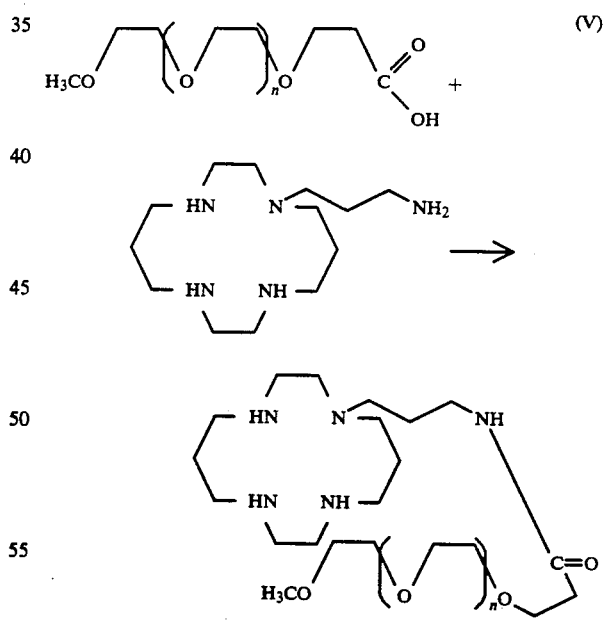

368 mg of the polymer (MW=5000), prepared by the method of K. Geckeler, E. Bayer, Polymer Bull. 3 (1980), 347, are dissolved with 7 mg of N(C₂H₅)₃, 17.6 mg of cyclam derivative from example 1, 15.2 mg of dicyclohexylcarbodiimide and 8.4 mg of 1-hydroxybenzotriazole in 5 ml of ethyl acetate, 5 ml of N,N-dimethylformamide and 10 drops of water. After the solution has been stirred for 16 h, the solvents are removed in vacuo and then the residue is subjected to ultrafiltration several times in aqueous solution. 345 mg of product (V)

(90%) can be isolated from the concentrate (no definite melting point since it is a polymer).

b) Labeling of (V)

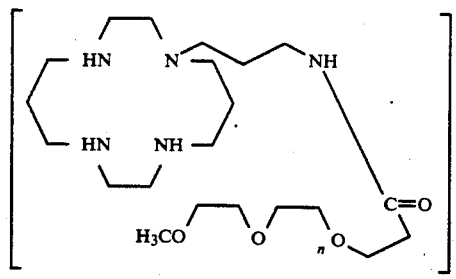

with $^{99m}Tc$ 8 mg of the polymer conjugate from example 3a) are dissolved in 0.5 ml of 0.9% NaCl, the pH is adjusted to 11 with 0.1 N NaOH, 1 ml of the PTP-Sn component described in German Offenlegungsschrift DE-A 3728599 (=EP-A 0271806 and US Ser. No. 130183) in example 7 is added (dissolved in 0.9% NaCl), and then 0.3 ml of $^{99}TcO_4$ solution (about 59 MBq of $^{99m}Tc$) is added. After 5 minutes at room temperature the pH is about 7. Thin-layer chromatography comparing with unsubstituted cyclam, free pertechnetate, the starting polymer and the PTP component, each chromatographed under the same conditions 5 minutes after addition of pertechnetate, revealed: about 10% of the $^{99m}Tc$ employed is bound to the polymer conjugate. The chromatography data on which this result is based are summarized in Table 1.

(Chromatography systems
  ITLC SG/methyl ethyl ketone
  ITLC SG/2 M $Na_2CO_3$
  Cellulose on Al/10% $NH_4OCCH_3$;
  $CH_3OH$
  1:1
  Whatman 1 paper/0.9% NaCl
  ITLC SG/0.5 M $NH_4OOCCH_3$)

EXAMPLE 5

Preparation of 2-hydroxymethyl-1,4,8,11-tetraazacyclotetradecane tetrahydrobromide

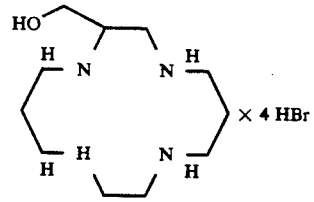

a) and b) The starting compound $NaTsN-(CH_2)_3-NTs-(CH_2)_2-NTs-(CH_2)_3-NTsNa$ is synthesized in analogy to example 2a) and b), merely the N,N'-di(aminoethyl)-1,3,-propanediamine being replaced by N,N'-di(aminopropyl)-1,2-ethylenediamine.

c) Synthesis of 1-phenoxymethyl-1,2-ethanediol

Phenyl glycidyl ether is prepared by the literature method of D. M. Dishong, C. J. Diamond, M. I. Cinoman, G. W. Gokel, J. Am. Chem. Soc. 105 (1983), 586-593.

d) Preparation of 1-phenoxymethyl-1,2-ethanediol ditosylate 5g of the starting diol (c) are introduced into 25 ml of pyridine, and 10.5 g of p-toluenesulfonyl chloride are added (slightly exothermic reaction). A precipitate appears after about 30 minutes. The mixture is stirred further at room temperature for 5 h and left to stand for 20 h, and then the pyridine is removed in vacuo. The residue is taken up in 2 N HCl, the solution is extracted 2× with diethyl ether, the ethereal phases are dried with $Na_2SO_4$ and filtered, and the product is obtained by evaporation. Yield 11.2 g of solid (83% of theory). Identification by $^1H$ NMR ($CDCl_3$) and thinlayer chromatography (silica gel, $CH_2Cl_2$, Rf=0.6).

e) Cyclization to give 2-phenoxymethyl-1,4,8,11-tetratosyl-1,4,8,11-tetraazacyclotetradecane 8.53 g of the 1,12-disodium salt of 1,5,8,12- tetratosyl-1,5,8,12-tetraazadodecane (as described under b)) are introduced into about 40 ml of N,N-dimethylformamide (DMF), the mixture is heated to 100° C., and then a

TABLE 1

| Chromatography Substance system | ITLC SG methyl ethyl ketone | ITLC SG 2M $Na_2CO_3$ | Cellulose/Al 10% $NH_4OAc$:MeOH 1:1 | Whatman/ 0.9% NaCl | ITLC SG 0,5M $NH_4OAc$ |
|---|---|---|---|---|---|
| $^{99m}Tc$-PEG | Rf = 0 43.2%<br>Rf = 1 56.8% | Rf = 0.6–1 100% | Rf = 0.1 97.1%<br>Rf = 0.7 2.9% | Rf = 0.1 98.3%<br>Rf = 0.8 1.4% | Rf = 0.1 11.4%<br>Rf = 0.2 18.1%<br>Rf = 1 70.5% |
| $^{99m}Tc$-PEG —COOH | Rf = 0<br>Rf = 0 67.2%<br>Rf = 32.8% | Rf = 0<br>Rf = 0.6–1 100% | Rf = 1 Rf = 1<br>Rf = 0.1 98.0%<br>Rf = 0.7 2.0% | Rf = 1<br>Rf = 0.1 96.8%<br>Rf = 0.8 3.2% | Rf = 0–0.3<br>Rf = 0.1 23.7%<br>Rf = 0.2 37.6%<br>Rf = 1 48.7% |
| $^{99m}Tc$-PEG —$NH_2$ Propylcyclam | Rf = 0<br>Rf = 0 78.6%<br>Rf = 1 21.4% | Rf = 0<br>Rf = 0 9.5%<br>Rf = 0.2–0.9 90.5% | Rf = 1<br>Rf = 0.1 45.6%<br>Rf = 0.7–0.9 54.4% | Rf = 1<br>Rf = 0.1 40.2%<br>Rf = 0.9 59.8% | Rf = 0–0.2<br>Rf = 0.1 35.1%<br>Rf = 0.2 37.6%<br>Rf = 1 27.3% |
| $^{99m}Tc$-Cyclam | Rf = 0<br>Rf = 0.1–0.2 100% | Rf = 0<br>Rf = 0 1.5%<br>Rf = 0.7–6 98.5% | Rf = 0.7–1<br>Rf = 0.9 100% | Rf = 0.8–1<br>Rf = 0.1 1.2%<br>Rf = 0.4 98.8% | Rf = 0–0.1<br>Rf = 0–0.3 15.6%<br>Rf = 0.3–0.9 84.4% |
| $^{99m}Tc$-PTP | Rf = 0–0.2<br>Rf = 0 98.9%<br>Rf = 1 1.1% | Rf = 1<br>Rf = 0 4.6%<br>Rf = 1 95.4% | Rf = 0.9<br>Rf = 0 100% | no stain possible<br>Rf = 0.1 100% | Rf = 0.3 Rf = 0.3<br>Rf = 0.1 29,2%<br>Rf = 0.1–0.8 41.3%<br>Rf = 0.8–1 10.0% |
| $^{99m}TcO_4-$ | Rf = 0 2.9%<br>Rf = 1 97.1% | Rf = 1 100% | Rf = 0.7 100% | Rf = 1 100% | Rf = 1 100% | solution of 4.75 g of 1-phenoxymethyl-1,2-ethanediol ditosylate in 40 ml of DMF is added dropwise. The mixture is stirred further at 100° C. for 6 h, followed by stirring at 20° C. for 20 h. Then about 200 ml of H$_2$O are added dropwise, the mixture is stirred vigorously for one hour (gummy precipitate), solid NaCl is added to salt out, and the white precipitate is filtered off. The filter cake is washed several times with water and then dried in vacuo. A little more product can be isolated from the mother liquor by further addition of water. Yield 4.7 g of white solid, corresponding to 50% of theory. Characterization by thin-layer chromatography (silica gel, ethyl acetate, Rf=0.8) and $^1$H NMR (CDCl$_3$).

f) Detosylation of 2-phenoxymethyl-1,4,8,11-tetratosyl-1,4,8,11-tetraazacyclotetradecane to give 2-hydroxymethyl-1,4,8,11-tetraazacyclotetradecane tetrahydrobromide.

The tetratosylated starting compound (10.8 g) is refluxed in 80 ml of 48% HBr +80 ml of glacial acetic acid for 3 days, left to stand at room temperature for 1 day and then taken up in CH$_2$Cl$_2$/H$_2$O, the organic phase is washed once with H$_2$O, and then the aqueous solution is extracted 5 times with 100 ml of CH$_2$Cl$_2$ each time (until the CH$_2$Cl$_2$ is colorless), and the aqueous phase is evaporated. The residue (dried in vacuo) is triturated 13 times in an ultrasonic bath with portions of CH$_2$Cl$_2$ totalling 800 ml until a yellowish white powdery residue remains. Drying in vacuo yields a product which corresponds to 2-hydroxymethyl-1,4,8,11-tetraazacyclotetradecane tetrahydrobromide with one tosyl group (NMR). This product is added to 100 ml of glacial acetic acid saturated with HBr gas and refluxed for 4 days. The crude product precipitates as a yellowish gray solid which is passed over a strongly basic anion exchanger (eluting with H$_2$O) in order to remove acetic acid. A mass spectrum shows M$^+$=230 and fragments at m/e=200 (cyclam) with m/e=174 (open-chain starting material). C, H, N analysis: 21.8% C, 5.3% H, 9.9% N, 58.7% Br, calculated for 2-hydroxymethyl-1,4,8,11-tetraazacyclotetradecane tetrahydrobromide: 23.8% C, 5.4% H, 10.1% N, 57.7% Br. The 1H NMR also shows 2-hydroxymethyl-1,4,8,11-tetraazacyclotetradecane tetrahydrobromide, with the 2-hydroxymethyl-1,4,8,11-tetraazacyclotetradecane tetrahydrobromide differing from the open-chain starting compound (in D$_2$O) mainly by a change in the integral ratio. The product (900 mg yield =34%) can be purified again by preparative HPLC (RP8 column, methanol/H$_2$O/HCl/ pH 2.7 with a mixing gradient, elution time 8-10 minutes).

EXAMPLE 6

Labeling of

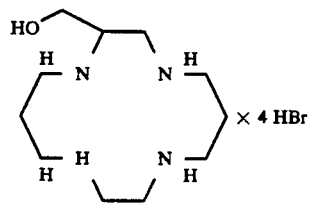

with $^{99m}$Tc 1 mg of 2-hydroxymethyl-1,4,8,11-tetraazacyclotetradecane tetrahydrobromide is dissolved in 1 ml of 0.9% NaCl. 0.1 ml of a solution of 1 mg of SnCl$_2$×5 H$_2$O in 1 ml of 0.1 N HCl is added, and the pH is adjusted to pH 5-6 with 0.1 ml of 0.1 N NaOH. 0.15 ml of $^{99m}$Tc eluate is added and then the activity of the solution is determined. It is 79.12 MBq/ml. 30 minutes later, ITLC-SG (2×10 cm strips) chromatography is carried out. Two samples are chromatographed at the same time, one in methyl ethyl ketone (free $^{99m}$TcO$_4$ migrates with the front), and one in 2 M Na$_2$CO$_3$ (colloidal $^{99m}$TcO$_4$ remains at the start). In methyl ethyl ketone all the radioactivity appears at Rf=0.43, in Na$_2$CO$_3$ about 90% of the radioactivity appears at Rf=1.0, the remainder is spread between Rf=0.4 and 1.0. This means that >90% of the technetium is complexed.

We claim:

1. A method for labeling a substance with technetium or rhenium isotopes, which comprises the steps of:
   a) reacting the substance to be labeled with a compound selected from the group of compounds of the formula I or II

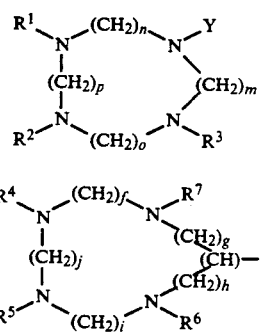

in which

R$^1$, R$^2$, R$^3$, R$^4$, R$^5$, R$^6$ and R$^7$ are identical or different and denote hydrogen, C$_1$—C$_4$-alkyl or aryl or aryl-C$_1$-C$_4$-alkyl, and m, n, o, p, f, h, i and j are identical or different and denote 1, 2, 3 or 4 and g denotes 0, 1, 2, 3 or 4, and Y denotes a group of the formula —X—NH$_2$, —X—NCS, —X—COOH, —X—OH, —X—N$_2$+ or —X—COCl or a group of the formula —X—Z, where Z denotes fluorine, chlorine, bromine or iodine, and X denotes an alkylene group having 1 to 40 carbon atoms, or X denotes an ortho-, meta- or para-phenylene or an ortho-, meta- or para-phenylenemethyl group, the substance having a reactive group which reacts with a reactive group on the exocyclic side-chain of the compound of the formula I or II, with formation of a chemical bond, and b) labeling the resulting compound with technetium-99m, rhenium-186 or rhenium-188 by adding to it pertechnetate-99m, perrhenate-186 or perrhenate-188 and a reducing agent for the pertechnetate or perrhenate.

2. The method as claimed in claim 1, wherein R$^1$, R$^2$, R$^3$, R$^4$, R$^5$, R$^6$ and R$^7$ are identical or different and denote hydrogen or C$_1$—C$_4$-alkyl, and m, n, o, p, f, i and j are identical or different and denote 2 or 3, and g denotes 0, 1 or 2, and h denotes 1 or 2, and Y denotes a group of the formula —X—NH$_2$, —X—NCS, —X—COOH, —X—OH, —X—N$_2$+ or —X—COCl or a group of the formula —X—Z, where Z denotes fluorine, chlorine, bromine or iodine, and X denotes an alkylene group having 1 to 20 carbon atoms.

3. The method as claimed in claim 1, wherein $R^1$, $R^2$, $R^3$, $R^4$, $R^5$, $R^6$ and $R^7$ denote hydrogen, and m, p and j denote 3, and n, o, f and i denote 2, and g and h denote 1, and Y denotes a group of the formula —X—NH$_2$ or —X—OH, where X denotes an alkylene group having 1 to 15 carbon atoms.

4. The method as claimed in claim 1, wherein the reactive group on the substance to e labeled is an —NH$_2$, —COOH, —COCl, —OH or —NH—NH$_2$ group.

5. The method as claimed in claim 1, wherein the substance to be labeled is a protein, a sugar, a fatty acid, a lipid, a steroid or a polymer, the polymer containing at least one side-chain of the formula —B—NH$_2$, —B—COOH, —B—NH—NH$_2$, —B—COCl or —B—OH, where B represents an o-, m- or p-arylene radical or an alkylene chain having 1 to 40 carbon atoms which, in the case of a $C_2$–$C_{40}$-alkylene chain, can have one or more methylene units of the chain replaced by an —NH—, —NH—CO—, —CO—NH—, —CO—O— or —O—CO— unit, and where the polymer has a molecular weight of from 1000 to 200,000 daltons.

6. The method as claimed in claim 5, wherein the protein to be labeled is an antibody, an antibody fragment, a monoclonal antibody, a monoclonal antibody fragment (F(ab')$_2$ or F(ab') fragment), an enzyme, a hormone, fibrinogen or human serum albumin.

7. A method for labeling a substance with technetium or rhenium isotopes, which comprises the steps of:
a) preparing a technetium-99m, rhenium-186 or rhenium-188 complex by reacting a compound selected from the group consisting of compounds of the formula I or II

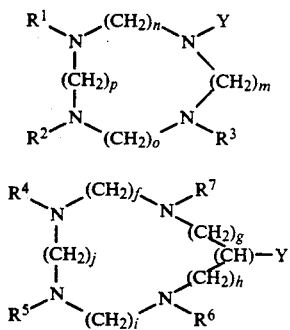

in which
$R^1$, $R^2$, $R^3$, $R^4$, $R^5$, $R^6$ and $R^7$ are identical or different and denote hydrogen, $C_1$–$C_4$-alkyl or aryl or aryl-$C_1$–$C_4$-alkyl, and
m, n, o, p, f, h, i and j are identical or different and denote 1, 2, 3 or 4 and g denotes 0, 1, 2, 3 or 4,
and denotes a group of the formula —X—NH$_2$, —X—NCS, —X—COOH, —X—OH, —X—N$_2$+ or —X—COCl or a group of the formula —X—Z, where Z denotes fluorine, chlorine, bromine or iodine, and X denotes an alkylene group having 1 to 40 carbon atoms, or X denotes an ortho-, meta- or para-phenylene or an ortho-, meta- or para-phenylenemethyl group
with pertechnetate-99m, perrhenate-186 or perrhenate-188 and a reducing agent for the pertechnetate or perrhenate, the substance having a reactive group which react with a reactive group on an exocyclic side-chain of the compound of formula I or II, with the formation of a chemical bond; and
b) reacting the resulting technetium-99m, rhenium-186 or rhenium-188 complex with the substance to the labeled.

8. The method as claimed in claim 7, wherein $R^1$, $R^2$, $R^3$, $R^4$, $R^5$, $R^6$ and $R^7$ are identical or different and denote hydrogen or $C_1$–$C_4$-alkyl, and m, n, o, p, f, i and j are identical or different and denote 2 or 3, and g denotes 0, 1 or 2, and h denotes 1 or 2, and Y denotes a group of the formula —X—H$_2$, —X—NCS, —X—COOH, —X—OH, —X—N$_2$+ or —X—COCl or a group of the formula —X—Z, where Z denotes fluorine, chlorine, bromine or iodine, and X denotes an alkylene group having 1 to 20 carbon atoms.

9. The method as claimed in claim 7, wherein $R^1$, $R^2$, $R^3$, $R^4$, $R^5$, $R^6$ and $R^7$ denote hydrogen, and m, p and j denote 3, and n, o, f and i denote 2, and g and h denote 1, and Y denotes a group of the formula —X—NH$_2$ or —X—OH, where X denotes an alkylene group having 1 to 15 carbon atoms.

10. The method as claimed in claim 7, wherein the reactive group on the substance to be labeled is an —NH$_2$, —COOH, —COCl, —OH or —NH—NH$_2$ group.

11. The method as claimed in claim 7, wherein the substance to be labeled is a protein, a sugar, a fatty acid, a lipid, a steroid or a polymer, the polymer containing at least one side-chain of the formula —B —NH$_2$, —B—COOH, —B—NH—NH$_2$, —B—COCl or —B—OH, where B represents an o-, m- or p-arylene radical or an alkylene chain having 1 to 40 carbon atoms which, in the case of a $C_2$-$C_{40}$-alkylene chain, can have one or more methylene units of the chain replaced by an —NH—, —NH—CO—, —CO—NH—, —CO—O— or —O—CO— unit, and where the polymer has a molecular weight of from 1000 to 200,000 daltons.

12. The method as claimed in claim 11, wherein the protein to be labeled is an antibody, an antibody fragment, a monoclonal antibody, a monoclonal antibody fragment (F(ab')$_2$ or F(ab') fragment), an enzyme, a hormone, fibrinogen or human serum albumin.

* * * * *

UNITED STATES PATENT AND TRADEMARK OFFICE
CERTIFICATE OF CORRECTION

PATENT NO. : 5,219,555
DATED : JUNE 15, 1993
INVENTOR(S) : KARL-HEINZ BREMER ET AL.

It is certified that error appears in the above-identified patent and that said Letters Patent is hereby corrected as shown below:

Claim 2, column 16, line 67, $-X-N_2+$ should read $-X-N_2^+$

Claim 4, column 17, line 10, change "e" to --be--.

Claim 7, column 18, line 12, change "react" to --reacts--.

Claim 7, column 18, line 17, before "labeled", change "the" to --be--.

Claim 8, column 18, line 23, $-X-H_2$ should read $-X-NH_2$

Claim 8, column 18, line 24, $-X-N_2+$ should read $-X-N_2^+$

Signed and Sealed this

Fifth Day of July, 1994

BRUCE LEHMAN

Attest:

Attesting Officer

Commissioner of Patents and Trademarks